(12) United States Patent
Magne et al.

(10) Patent No.: US 9,664,609 B2
(45) Date of Patent: May 30, 2017

(54) DEVICE FOR MEASURING THE CORROSION IN A METALLIC STRUCTURE OR A STRUCTURE COMPRISING AT LEAST ONE METALLIC REINFORCEMENT, ASSOCIATED USES AND METHOD

(71) Applicant: Commissariat à l'énergie atomique et aux énergies alternatives, Paris (FR)

(72) Inventors: Sylvain Magne, Chatillon (FR); Shamyr Ali Alvarez, Paris (FR); Pierre Ferdinand, Houilles (FR); Stéphane Rougeault, Sceaux (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 107 days.

(21) Appl. No.: 14/408,356

(22) PCT Filed: Jun. 17, 2013

(86) PCT No.: PCT/EP2013/062489
§ 371 (c)(1),
(2) Date: Dec. 16, 2014

(87) PCT Pub. No.: WO2013/189877
PCT Pub. Date: Dec. 27, 2013

(65) Prior Publication Data
US 2015/0168289 A1    Jun. 18, 2015

(30) Foreign Application Priority Data
Jun. 18, 2012 (FR) ...................... 12 55692

(51) Int. Cl.
*G01B 11/16* (2006.01)
*G01N 17/04* (2006.01)
*G01B 17/00* (2006.01)

(52) U.S. Cl.
CPC ............. *G01N 17/04* (2013.01); *G01B 11/16* (2013.01); *G01B 17/00* (2013.01)

(58) Field of Classification Search
CPC ......... G01N 17/04; G01N 17/00; G01B 11/16
(Continued)

(56) References Cited

U.S. PATENT DOCUMENTS

| 2006/0042363 A1* | 3/2006 | Howells | G01N 17/04 73/86 |
| 2006/0162432 A1* | 7/2006 | Jaralla | G01N 17/04 73/86 |

(Continued)

OTHER PUBLICATIONS

Simon K. T. Grattan et al., "Monitoring of Corrosion in Structural Reinforcing Bars: Performance Comparison Using in Situ Fiber-Optic and Electric Wire Strain Gauge Systems" IEEE Sensors Journal, vol. 9, No. 11, Nov. 2009.
(Continued)

*Primary Examiner* — Hina F Ayub
(74) *Attorney, Agent, or Firm* — Pearne & Gordon, LLP

(57) ABSTRACT

Device for measuring corrosion in a structure. It comprises: at least one assembly comprising a metallic part (2) intended to be fixed to the structure and able to deform under the effect of corrosion and/or a thermomechanical variation, and transduction means (4) comprising an optical fibre (3) fixed to the metallic part in a prestressed state, the transduction means being able to modify light propagating in the fibre under the effect of a stress applied to the fibre; means for measuring and processing the spectral responses supplied by the transduction means of said at least one assembly.
The metallic part is segmented longitudinally in order to form an alternation of segments covered by a corrosion-protection material (8) and uncovered segments, in order to distinguish the thermomechanical influence of the structure from the mechanical effects caused by corrosion.

14 Claims, 5 Drawing Sheets

(58) Field of Classification Search
USPC .......................................................... 356/32
See application file for complete search history.

(56) References Cited

U.S. PATENT DOCUMENTS

| | | | |
|---|---|---|---|
| 2007/0019898 A1* | 1/2007 | Chimenti | G01L 1/246 385/12 |
| 2007/0284112 A1 | 12/2007 | Magne | |
| 2008/0129985 A1 | 6/2008 | Laffont | |
| 2008/0143344 A1* | 6/2008 | Focia | G01M 5/0025 324/642 |
| 2008/0204706 A1 | 8/2008 | Magne | |
| 2008/0217172 A1* | 9/2008 | Chiang | G01N 17/04 204/404 |
| 2011/0170823 A1* | 7/2011 | Xia | G01D 5/35303 385/12 |
| 2012/0035885 A1* | 2/2012 | Tarassenko | G01H 1/006 702/183 |

OTHER PUBLICATIONS

Mark Froggat et al., "High-spatial-resolution distributed strain measurement in optical fiber with Rayleigh scatter" Applied Optics, vol. 37, No. 10, Apr. 1, 1998.
Mark Froggat et al., "Distributed Strain and Temperature Discrimination in Unaltered Polarization Maintaining Fiber" Conference, Optical Fiber Sensors, Cancun Mexico, Oct. 23, 2006.
Pierre Ferdinand, "Capteurs a fibres optiques a reseaux de Bragg" Techniques de l'ingenieur 2001, R6735, 1-24.
Jung-Ryul Lee et al. "Technical Design Note: A structural corrosion-monitorning sensor based on a pair of prestrained fiber Bragg gratings", Measurement Science and Technology, vol. 21, No. 1, Jan. 16, 2009.
Mousumi Majumder et al. "Fibre Bragg gratings in structural health monitoring—Present status and application", Sensors and Actuators A: Physical, vol. 147, No. 1, Apr. 22, 2008.
P. Moyo et al. "Development of fiber Bragg grating sensors for monitoring civil infrastructure", Engineering Structures, vol. 27, No. 12, Jul. 11, 2005.
Yung Bin Lin et al. "The health monitoring of a prestressed concrete beam by using fiber Bragg grating sensors" Smart Materials and Structures, vol. 13, No. 4, May 18, 2004.
International Search Report issued in Application No. PCT/EP2013/062489 dated Jul. 22, 2013.
Written Opinion issued in Application No. PCT/EP2013/062489 dated Jul. 22, 2013.
French Search Report issued in Application No. FR 12 55692 dated Nov. 14, 2012.

* cited by examiner

DEVICE FOR MEASURING THE CORROSION IN A METALLIC STRUCTURE OR A STRUCTURE COMPRISING AT LEAST ONE METALLIC REINFORCEMENT, ASSOCIATED USES AND METHOD

TECHNICAL FIELD

The present invention relates to the field of the detection, measurement and control of corrosion in metallic structures or structures comprising at least one metallic reinforcement (in particular in reinforced-concrete structures).

It relates more particularly to a device for measuring the corrosion in a metallic structure or a structure comprising at least one metallic reinforcement, to the uses of this device and to a method associated with such a device.

In general terms, the present invention can be used for detecting corrosion in all types of structure liable to suffer corrosion, that is to say in metallic structures or structures comprising at least one metallic reinforcement (in particular reinforced-concrete structures).

The invention is therefore able to be used more particularly for detecting corrosion in civil engineering works (buildings, dams, bridges, tunnels, etc) or maritime transport (boats, etc), maritime structures and foundations of coastal or sea structures (dykes, jetties, offshore wind turbines and platforms, tidal-power plants, marine turbines, etc).

PRIOR ART

Detecting corrosion in metallic structures or structures comprising at least one metallic reinforcement, in particular reinforced-concrete structures, is essential.

This is because, when they are attacked by corrosion, these structures are weakened, which may imperil the safety of property and persons and have considerable socioeconomic consequences.

Since a massive deconstruction followed by reconstruction of the corroded structures would give rise to excessively great costs, it is necessary to proceed with maintenance of these structures in order to identify corroded structures and thus be able to repair them in time.

Currently, this maintenance is programmed periodically and routinely. However, the drawback of programmed maintenance (schedule-driven maintenance) is that it requires periodically inspecting surfaces of very large structures, which may be as great as several tens of thousands of $m^2$, which represents a considerable amount of work.

Furthermore, in the particular case of a reinforced-concrete structure, it is rarely possible to anticipate the actual state of the structure only from a visual analysis of its external surface. It therefore proves necessary to have recourse to means of inspection of the structure in depth, or in its buried foundations, which therefore makes the inspection thereof and the time necessary for the inspection thereof more complex.

Locating the corrosion and estimating its degree of development are therefore made tricky and often involve great uncertainty.

Because of the constant increase in costs relating to the maintenance and restoration of structures damaged by corrosion, it is therefore sought more and more to favour a conditional repair strategy (condition-based maintenance, or CBM), rather than periodic.

The principle of condition-based maintenance (CBM) is to optimise interventions where they are actually necessary and thus avoid routine, lengthy and expensive analysis of the structures and infrastructures.

However, the efficacy of this advanced maintenance strategy relies on obtaining a precise and reliable mapping of the global state of corrosion of a structure, in order to selectively act on areas identified as "at risk". For this purpose, it is necessary to make measurements that are reliable on a meteorological level (rather than only probabilistically influenced), distributed (rather than at isolated points), in situ (rather than from the surface, when the parts liable to corrode are situated inside the structure), on demand and/or condition-based (rather than programmed) and, if possible, minimising the socioeconomic impact of the maintenance on the wear of the infrastructure and optimising the cost of such maintenance.

Among the sensors that are currently used for detecting corrosion in the context of programmed maintenance, those that would be able to suit implementation in the context of condition-based maintenance are rare, the majority of these sensors providing probabilistic or isolated measurements and/or measurements obtained from the surface of the structure.

Among the potential candidates, the inventors have focused on sensors that make it possible to make a direct measurement of corrosion, and in particular on fibre optic sensors (FOSs), where the principle of measuring corrosion is based on a mecano-optical conversion.

This is the case, for example, with the sensor described by Grattan et al. in their article "Monitoring of corrosion in structural reinforcing bars: performance comparison using in situ fiber-optic and electric wire strain gauge systems", *IEEE Sensors Journal* 2009, 9(11), 1494-1502 (reference [1]).

In this article, Grattan et al. describe a method for detecting the mechanical effects of corrosion in an iron reinforcement situated in reinforced concrete, by virtue of the use of a Bragg grating sensor sensitive to the stresses caused by an expansion of the corrosion products (iron oxides). This sensor comprises an optical fibre, as well as Bragg gratings that are photo-inscribed in the core of the optical fibre and serve as transducers (corrosion-deformation conversion). This optical fibre thus transformed is, by means of an epoxy resin and in the direction of its length, bonded to an iron reinforcement the corrosion of which it is wished to monitor. The reinforcement equipped with the optical fibre is finally disposed in a concrete test piece and the structure thus obtained is subjected to accelerated corrosion.

At the end of this experiment, Grattan et al. show a shift in the Bragg wavelength that is caused by the expansion of the corrosion products (compression or traction).

The drawback of this sensor is that the measurements that it makes it possible to obtain include both the deformations due to the global thermomechanical effects applied to the support (reinforcement) on which it is fixed and those due to the local mechanical effects particular to the corrosion. The measurements obtained are therefore not sufficiently distinctive and precise.

Another example of a fibre optic corrosion sensor is detailed by the authors Lee et al. in their article "A structural corrosion-monitoring sensor based on a pair of prestrained fiber Bragg gratings", *Measurement Science and Technology* 2010, 21(1), 017002.1-017002.7 (reference [2]).

In this article Lee et al. describe a fibre optic corrosion sensor (FOS) based on the use of a Bragg grating. This sensor is composed of an optical fibre comprising a Bragg grating and a sacrificial metal plate intended to be corroded.

The optical fibre is first of all pretensioned by means of mechanical pre-tension elements and is then bonded to the sacrificial metal plate using an epoxy resin. After polymerisation of the resin, the mechanical pre-tension elements are removed. A state of equilibrium then appears between the force exerted by the (pre-tensioned) fibre and that exerted in reaction by the plate (compressed), which is a function of the respective rigidities of the fibre and plate.

In an example embodiment described by Lee et al., the fibre optic sensor (FOS) is 34 mm long. The sacrificial plate is 34 mm long, the Bragg grating is 10 mm long and each bonding region extends over 10 mm. In these bonding regions, the sacrificial plate is coated with an acrylic layer in order to protect it against corrosion. Thus only the middle part of the FOS (14 mm) is exposed to the environment. In the state of equilibrium, a shift in length of 2 nm is observed in the spectral response of the Bragg grating for this particular FOS (deformation equivalent to approximately 1670 micro deformations); under the action of the corrosion, the mass and the cross section of the sacrificial plate decrease and the reduction in rigidity consequent on the corrosion causes a change to the value of the spectral shift.

Lee et al. also describe a thermomechanical compensation method based on the use of two fibre optic sensors each comprising a Bragg grating, these two sensors being connected in series or in parallel and placed parallel to each other, one of the sensors being entirely protected from corrosion by the application of an acrylic coating over its entire surface, while the other sensor is exposed to the environment. Thus, unlike the FOS described in reference [1], the particular assembly described in reference [2] makes it possible to use thermomechanical compensation.

The drawback of the solution proposed by the authors Lee et al. for distinguishing the global thermomechanical effects (applied to the metallic support to which the optical fibre is fixed (sacrificial metal plate)) from the local mechanical effects particular to the corrosion is that it is complex since it requires the use of a supplementary FOS protected from corrosion and placed parallel to the first FOS.

Another drawback of the particular assembly proposed in reference [2] is that it makes it possible to obtain only an isolated measurement of the corrosion. However, in order to guarantee optimum monitoring of the progression of corrosion within a structure, it would be necessary to be able to have a multitude of measuring points, which would make it necessary to considerably increase the number of sensors (since there are two sensors per measuring point). In concrete terms this is not possible since the number of measuring points is limited for technical and economic reasons (cost of the sensor, but especially of its deployment within the structure and the necessary connections). Such an assembly would therefore not be suitable for implementing condition-based maintenance (CBM).

In the light of the drawbacks of the fibre optic corrosion sensors (FOS) described above, the inventors set out to design a corrosion-measuring device that makes it possible to obtain a plurality of corrosion measuring points while simplifying the use of thermomechanical compensation, thus making it possible to use such a device in the context of condition-based maintenance.

DISCLOSURE OF THE INVENTION

This aim and others are achieved by the invention, which proposes firstly a device for measuring corrosion in a metallic structure or a structure comprising at least one metallic reinforcement, said device comprising:

at least one assembly that comprises:
- a metallic part intended to be mechanically secured to the structure, said metallic part extending in a longitudinal direction and being able to undergo stresses under the effect of corrosion and/or a thermomechanical variation;
- transduction means comprising an optical fibre, the optical fibre being fixed to the metallic part in a prestressed state under compression so as to undergo the stresses suffered by the metallic part, said transduction means being able to modify light propagating in the optical fibre under the effect of the stresses applied to the optical fibre;

measurement and processing means for measuring and processing the spectral responses supplied by the transduction means of said at least one assembly.

The device according to the invention is characterised in that the metallic part of said at least one assembly has an alternation of first and second portions, arranged in the longitudinal direction of the metallic part, each of the first and second portions being associated with at least one of the transduction means and only the first portions being covered with a layer of corrosion-protection material, so that the spectral responses supplied by the transduction means associated with the first portions are able to translate the application of a thermomechanical stress to the first portions, while the spectral responses supplied by the transduction means associated with the second portions are able to translate the application of a thermomechanical stress and/or a corrosion to the second portions, said layer of corrosion-protection material comprising a groove in which the optical fibre is housed.

The device according to the invention is also characterised in that the measurement and processing means further comprise means for comparing the spectral responses supplied by the transduction means associated with the first portions and those supplied by the transduction means associated with the second portions, in order to establish a corrosion profile of the metallic part. In fact, the device according to the invention enables us to differentiate, among the stresses, those that are due to corrosion from those that are due to thermomechanical stresses. It is thus possible to establish a corrosion profile of the metallic part and a thermomechanical profile that are separate from each other.

In order to be mechanically secured to the structure, the metallic may for example be screwed to the structure, in particular when the structure is metallic; it may also be incorporated or embedded in the body of the structure, when the body of the structure is not metallic and the structure comprises at least one metallic reinforcement, as is the case for example with a reinforced-concrete structure.

In the device according to the invention, the segmentation in the longitudinal direction of the metallic part of the device makes it possible to obtain an alternation of portions covered with a corrosion-protection layer and portions not covered with a corrosion protection layer, these non-covered portions thus being able to be corroded in the presence of corrosive agents. This alternation makes it possible to distinguish the thermomechanical influence of the metallic part (loading, thermomechanical stresses due to the expansion of the structure) from the mechanical effects caused by the corrosion of this metallic part. It is thus possible to subtract the influence of the longitudinal deformation from the deformation caused by corrosion.

Moreover, in the device according to the invention, the optical fibre is in a prestressed state under compression. The fact that the optical fibre is in a prestressed state under compression enables us to detect the appearance of pit corrosion, this type of corrosion causing rupture in the cohesion of the metallic part to which the fibre is fixed and the relaxing of the prestressing applied to the optical fibre.

It should be noted that the metallic structure and the metallic reinforcement to which we refer in the present description may be made from a metal or a metal alloy.

Moreover, in the above and the following, the term "length", when it refers to an object (for example the metallic part of the first and second portions) means the dimension of said object in the longitudinal direction of this object.

Preferably the first (covered) portions of the metallic part have lengths of a few centimeters (that is to say typically from 1 cm to 5 cm) while the second (uncovered) portions of the metallic part have lengths from a few centimeters to a few decimeters (that is to say typically from 1 cm to 20 cm).

Since the values of the lengths of the first and second portions are much smaller than the thickness of the structure (thickness of a wall, for example, in the case of a civil engineering structure), it can be considered that two adjacent portions are subjected substantially to the same temperature and consequently that the temperature gradient existing between two adjacent portions is negligible. More particularly, the temperature gradient is almost zero when the instrumented metallic part that serves as a corrosion sensor is placed parallel to the surface of the structure (temperature gradient oriented transversely); as for the highest temperature gradient, this is obtained when the instrumented metallic part is placed perpendicular to the surface of the structure, aligned parallel to the gradient, which does not constitute the recommended implementation, but even in this unfavourable situation the effect of a temperature gradient can be ignored. By way of example, let us consider a temperature gradient of 10 K/m through the wall of a bridge, for example: the difference in temperature between a covered portion and an uncovered portion, adjacent and separated by 5 cm, is only 0.5 K, giving rise to a difference in deformation of only 10 microdeformations (approximately) between the two portions in question.

It should be noted that, in the above and in the following, we shall frequently use the expression "instrumented metallic part" to designate an assembly according to the invention formed by a metallic part and transduction means comprising at least one optical fibre fixed in a prestressed state under compression on the metallic part, for the purpose of simplifying the reading of the description.

According to a variant of the invention, for at least one assembly, the groove in which the optical fibre is housed is also present in the second portions of the metallic part, the groove being formed in the external surface of the metallic part.

With regard to the groove, whether this is only present in the layer of corrosion-protection material (at the first portions) or whether it is present both in this layer (at the first portions) and in the metallic part (at the second portions), it makes it possible to house the optical fibre and to provide mechanical protection for the fibre. By being housed in the groove, the optical fibre remains close to the interface formed by the metallic part and by the structure to be studied (iron/concrete interface, for example, in a reinforced-concrete structure comprising passive iron reinforcements) and can then provide early detection of corrosion while being mechanically protected.

According to a preferred embodiment of the invention, for at least one assembly, the first and second adjacent portions of the metallic part form a periodic pattern that is repeated in the longitudinal direction of the metallic part. According to this particular embodiment, the first and second portions of the metallic part, in addition to being arranged in alternation in the longitudinal direction, are also arranged periodically in this longitudinal direction. Thus the metallic part is segmented in the longitudinal direction in a periodic segmentation pattern M, with $M=I_1/(I_1+I_2)$, where $I_1$ is the length of an uncovered portion in the longitudinal direction and $I_2$ the length of a covered portion in the longitudinal direction, the uncovered portion and the covered portion being adjacent.

Advantageously, for at least one assembly, the prestressed state under compression of the optical fibre is obtained by means of the presence of a layer made from a thermoset material that covers the optical fibre and compresses it onto the metallic part when it cools.

It should be noted that a person skilled in the art will know what thermoset material he must choose if he wishes to obtain compression of the optical fibre, in particular according to the coefficient of thermal expansion of the fibre, since it is the difference existing between the coefficients of thermal expansion of the fibre and of the thermoset material that makes it possible to obtain the compression of the fibre.

It should also be noted that, when the optical fibre is housed in a groove (first portions and optionally second portions), compression thereof may be obtained by covering the layer with a thermoset material, which partially or completely fills in the groove: the optical fibre thus covered is then compressed in the groove by the thermoset material. Preferably, the optical fibre is entirely embedded in the thermoset material (for example a coating resin such as an epoxy resin).

The groove preferably has a millimetric or even sub-millimetric width. Preferably, the optical fibre that is housed in this groove is mono mode and has a diameter of around 150 micrometers (for example a fibre having a polyimide sheath).

According to a particular embodiment of the invention, the metallic part of each assembly of the device comprises shoulders arranged in the longitudinal direction of the metallic part. The shoulders serve to embed the metallic part in the body of the structure to be monitored in order to guarantee good mechanical coupling of the axial forces between the two materials. This is because the shoulders provide a sufficient absorption of force between the material of the structure to be monitored and the material of the metallic part. The presence of the shoulders proves to be necessary when the assembly or assemblies of the device according to the invention must be incorporated or embedded in the body of the structure to be monitored, as is the case for example with a reinforced-concrete structure. Moreover, in the case of a reinforced-concrete structure, the shoulders also serve as a protection for the optical fibre against external mechanical attacks (for example against the aggregates present in a reinforced-concrete structure).

Preferably, when the structure is metallic, the metallic part of each assembly is made from a material that is similar, preferably identical, to the material of the structure and, when the structure is not metallic and comprises at least one metallic reinforcement, the metallic part of each assembly is made from a material that is similar, preferably identical, to the material of the metallic reinforcement (for example the reinforcement used for reinforcing a reinforced-concrete structure). In fact it is preferable for the metallic material of the metallic part to have the same composition (the "same reference", for example FE 500, is also spoken of) as the metallic material of the reinforcements (or of the structure, when the structure is made from a metallic material). However, in practice, it may prove difficult to have exactly the same composition. It is in fact improbable that the instrumented metallic part of the device according the invention and the metallic reinforcements of a reinforced-concrete structure, for example, would come from the same casting. This is the reason why similar compositions are also spoken of, bearing in mind that the compositions must be as close as possible, and preferably be identical, so as to avoid the appearance of galvanic effect (consumable electrode).

Advantageously, for at least one assembly of the device, the transduction means consist of an optical fibre or Bragg gratings, photoinscribed in an optical fibre.

According to a first variant, when the transduction means consist of Bragg gratings photoinscribed in an optical fibre fixed to a metallic part, each of the first and second portions of this metallic part is associated with at least one Bragg grating and the measurement and processing means comprise an optoelectronic measuring system for measuring the Bragg wavelength characteristic of each of the Bragg gratings photoinscribed in the optical fibre. According to a second variant, when the transduction means consist of an optical fibre, the measurement and processing means apply a technique of measuring by Rayleigh reflectometry OFDR to this optical fibre, the measurement resolution of this technique being chosen so as to be centimetric and smaller that the smallest of the first and second portions of the metallic part to which the optical fibre is fixed. It should be noted that, when an OFDR measurement technique is used, the optical fibre serves simultaneously as a transducer and as a measurement channel.

According to a particular embodiment, the device according to the invention comprises several assemblies, said assemblies being connected in parallel and/or in series. By way of example, several assemblies may be connected orthogonally, placed in series and in parallel, spaced apart by a distance of around 1 meter for example, in order to cover a large surface area that may be as much as several thousands of square meters. It is also possible to place the assemblies at various depths within the structure to be checked to enable the operator to obtain information on the kinetics of an advance of the corrosion (advance of the carbonation or chloride front).

Another subject matter of the invention is use of a device as defined above for detecting corrosion in a structure comprising a main body, metallic or concrete, and one or more metallic reinforcements, at least one of the metallic reinforcements consisting of the metallic part of an assembly of said device.

The metallic part of the device according to the invention can thus replace one of the metallic reinforcements of a metallic or concrete structure, for example replace one of the passive reinforcements used to reinforce a reinforced-concrete structure. In this case, it is then preferable for the instrumented metallic part that serves as a corrosion sensor to fulfil the same reinforcement function as the passive reinforcement for which it is substituted and for it not to modify the structure reinforcement scheme. Furthermore, it is preferable for the metal making up the metallic part to be similar, and preferably identical, to that of the reinforcements of the structure, in order to avoid a galvanic effect (consumable electrode). It is possible for example to use metallic parts made from carbon steel in civil engineering structures reinforced by reinforcements of the same metal.

Another subject matter of the invention is the use of a device as defined above as a corrosion tell-tale for a metallic structure, the metallic part of each assembly of the device being fixed to the surface of the structure. In this case, it is preferable for the metallic part or parts of the device to be made from the same material as the metallic structure (usually based on aluminium alloys), in order to avoid a galvanic effect (consumable electrode).

Finally, a subject matter of the invention is a method for detecting and locating the corrosion on a metal part of an assembly of a device as defined above, said part being mechanically secured to a metallic structure or comprising at least one metallic reinforcement, the method comprising, for each assembly, the following steps:

measuring the change in amplitude of the spectral response over time for each of the first and second portions of the metallic part (this step makes it possible to monitor the change in deformation of the metallic part over time);

determining the contribution of the corrosion to the change in the amplitude of the spectral response over time by comparison between the amplitudes of spectral responses of first and second adjacent portions (this step makes it possible to differentiate the deformations of thermomechanical origin from the deformations due to corrosion, in order to isolate the component of the deformations solely due to corrosion);

if the contribution of the corrosion to the change in amplitude is greater, in absolute value, than a threshold value on at least one of the second portions of the metallic part, determining the presence of corrosion on said at least one second portion (by knowing on which second portion the corrosion takes place, it is possible to know the location of the corrosion on the metallic part); and optionally, determining the type of corrosion according to the sign of the change in amplitude (it is possible in fact to deduce the type of corrosion by means of the sign of the change in amplitude, which depends on the stress applied, which results either from a release of the compression prestress (corrosion by formation of chlorides in the metallic part, causing a pitting attack on the metallic part), or from a compression that is superimposed on the compression prestress (corrosion of the metallic part due to carbonation of the concrete, causing an expansion of the corrosion products (iron oxide)). It should be noted that, in metallic structures, the phenomenon of corrosion by carbonation does not exist; it is therefore possible to detect only the presence of pitting corrosion.

As the metallic part of each of the assemblies of the measuring device according to the invention is segmented in the longitudinal direction in an alternation of first and second portions and each of the first and second portions is associated with at least one transducer, it is possible to rapidly detect the appearance of corrosion at any point along the metallic part and to locate which portion of the metallic part is attacked by corrosion.

In the method according to the invention, either a Bragg wavelength shift or an OFDR frequency shift is measured, distributed over the whole of the metallic part of each of the assemblies of the device. These shifts are caused by mechanical effects related to the corrosion occurring on the second portions of the metallic part of each of the assemblies of the device (the second portions of the metallic part being not covered by a protective layer against corrosion and therefore being subject to corrosion), but also by thermomechanical effects imposed by the structure; it therefore proves necessary to distinguish these two effects in order to determine the presence and magnitude of the corrosion. The location and measurement of the amplitude of the corrosion along the metallic part of each of the assemblies of the device are determined by a computation method (weighting and subtraction) applied to the deformation profiles measured on the first portions and on the second portions.

When the optical fibre of the assembly is prestressed in compression on the metallic part, the second portions and the transduction means cooperate so that appearance of corrosion in at least one of the second portions of the metallic part results in an increase or reduction in the compression stress in at least one transducer associated with this second portion. In fact, depending on the corrosive agents in action in the structure, the corrosion is manifested by a release of the pre-established compression stress or by the appearance of an additional compression that is added to the pre-established compression.

The device according to the invention has many advantages.

First of all, unlike the FOSs described in the prior art, the device according to the invention supplies a spread (OFDR mode) or distributed (Bragg mode) measurement along each metallic part of the device, instrumented by an optical fibre.

The appearance of corrosion is manifested by a change in the stress profile applied to the optical fibre, detectable along the entire length of the metallic part to which the optical fibre is fixed. Corrosion is therefore detectable over the entire length of the metallic part (which is typically from a few meters to a few tens of meters) rather than only at one point.

The device according to the invention also makes it possible to monitor the progression of the corrosion all along each of the metallic parts of the device and in the long term.

The device according to the invention makes it possible to achieve a high spatial coverage compatible with the large exposed surface areas of the structures, such as civil engineering structures.

It also makes it possible to achieve an in situ and in depth diagnosis within the structure, as well as in its foundations, regions inaccessible to observation. This is because each assembly of the device (metallic part equipped with an optical fibre and transduction means) can be embedded in the structure to be monitored and it is possible to obtain an in situ measurement of the corrosion. The assembly or assemblies of the device can be embedded in the structure close to the surface and at various depths in the thickness of the structure, as well as in its foundations, thus allowing analysis of the change in corrosion over the long term.

Moreover, each metallic part of the device may take the place of a metallic reinforcement in a structure and keep the function of strengthening of this reinforcement.

Finally, the device according to the invention makes it possible to obtain information on the type of corrosion (chlorides or carbonation/sulfation), on its location in the structure and on its progression kinetics inside the structure (mainly the advance of the carbonation or chloride front).

Ultimately, the device according to the invention can therefore be used in the context of condition-based maintenance.

Another advantage of the device according to the invention is that its constituent elements are inexpensive and easy to install in the structure, which allows future savings in terms of maintenance cost of the structures justifying the deployment of such a device on a large scale in future civil engineering structures at the design stage.

The invention will be better understood and other advantages and particularities will emerge from a reading of the following description given by way of non-limitative example, accompanied by the appended figures.

BRIEF DESCRIPTION OF THE FIGURES

FIG. 2b depicts a view in cross section, along the straight line AA, of the assembly depicted in FIG. 2a.

FIG. 2c depicts a view in cross section, along the straight line BB, of the assembly depicted in FIG. 2a.

FIG. 4b depicts a view in cross section, along the straight line AA, of the assembly depicted in FIG. 4a.

FIG. 4c depicts a view in cross section, along the straight line BB, of the assembly depicted in FIG. 4a.

Figure 1:
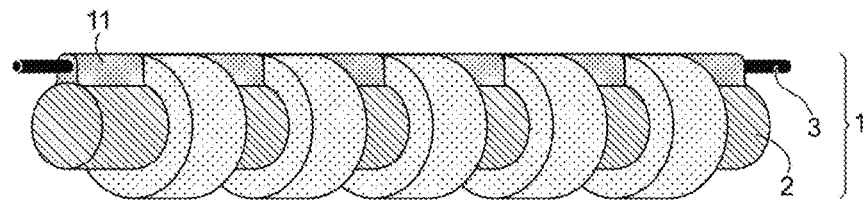
FIG. 1 depicts, schematically and in a longitudinal view, a first example embodiment of the assembly, depicted alone, of the measuring device according to the invention.

The various elements illustrated in the above figures are not shown to scale.

Also the same references are used to designate elements having substantially the same function.

DETAILED DISCLOSURE OF PARTICULAR EMBODIMENTS

1—Elements Constituting the Measuring Device According to the Invention

The measuring device 10 according to the invention comprises firstly at least one assembly 1 formed by a metallic part 2 that extends in a longitudinal direction, and transduction means 4 comprising an optical fibre 3, and secondly comprises measuring and processing means 5.

This assembly 1 is depicted in detail and according to several embodiments of the invention in FIGS. 1, 2a, 2c, 2b, 3, 4a, 4b and 4c.

In FIGS. 1, 2a, 2b and 2c, the metallic part 2 is a metallic bar with a constant diameter. On its surface there are disposed rings that are formed by covering certain portions of the surface of the metallic part (corresponding to the first portions 6) with a layer 8 made from a material for protection against corrosion. In these rings, a groove 9 is produced, in which an optical fibre 3 is placed. As can be seen in FIG. 1, the optical fibre 3 extends over the entire length of the metallic part.

The optical fibre 3 is fixed in a prestressed state under compression on the surface of the metallic part 2, this prestressed state under compression being able for example to be obtained by hot-bonding the optical fibre to the metallic part.

Figure 2A:
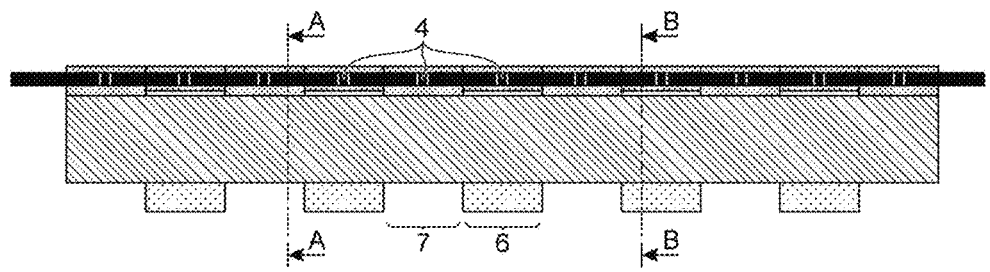
FIG. 2a depicts a view in longitudinal section of the assembly depicted in FIG. 1.
Figure 2B:
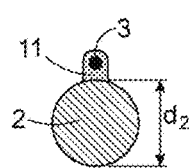
Figure 2C:
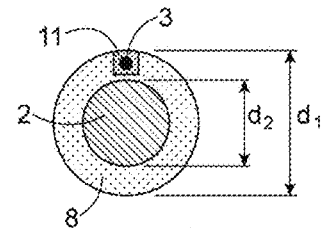

As can be seen in FIG. 2c, the optical fibre 3 is protected mechanically when it is prestressed under compression in the groove 9, that is to say when it is situated in the first portions 6 of the metallic part. When it is situated in the second portions 7 of the metallic part, the fibre is protected mechanically by the layer 11 that encloses the fibre and is used to stress it under compression (FIG. 2b).

In FIGS. 3, 4a, 4b and 4c, the metallic part 2 is a metallic bar having a diameter $d_1$ in the second portions 7 and a diameter $d_2$ less than $d_1$ in the first portions 6 (portions covered by the corrosion-protection layer 8). The optical fibre 3 is housed in a groove 9 that extends between the two longitudinal ends of the metallic part.

Figure 4A:
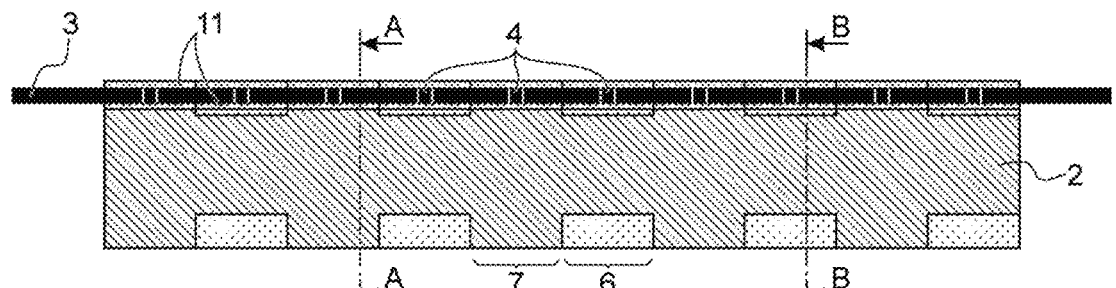
FIG. 4a depicts a view in longitudinal section of the assembly depicted in FIG. 3.
Figure 4B:
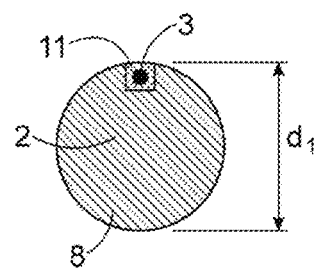
Figure 4C:
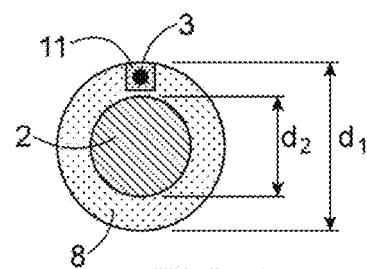

As can be seen in FIGS. 4a, 4b and 4c, this groove is formed in the external surface of the metallic part when in the second portions 7 of the metallic part (portions intended to suffer corrosion) (FIG. 4b), whereas it is formed in the corrosion-protection layer 8 when in the first portion 6 of the metallic part (FIG. 4c).

In the first and second portions, the optical fibre is covered with a layer 11 that compresses the optical fibre towards the metallic part and embeds it in the groove.

In FIGS. 2a and 4a (as well as in FIGS. 5c and 6e below), it can be seen that there is indeed at least one transduction means 4 per first portions 6 and per second portions 7.

Figure 3:
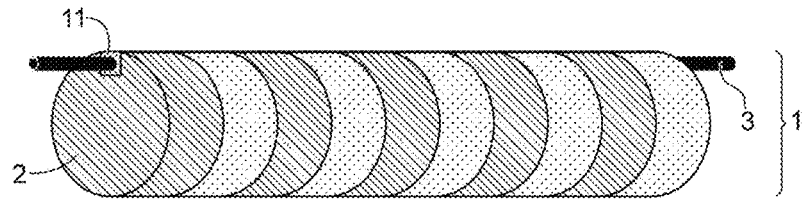
FIG. 3 depicts, schematically and in a longitudinal view, a second example embodiment of the assembly, depicted alone, of the measuring device according to the invention.
Figure 6A:
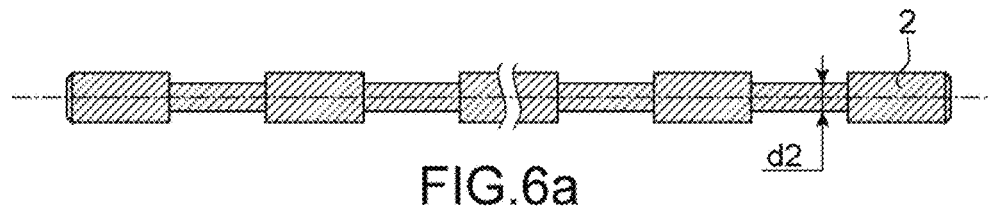
FIGS. 6a to 6e depict the steps of the method for producing an assembly of the device according to the invention, according to another particular embodiment.
Figure 6B:
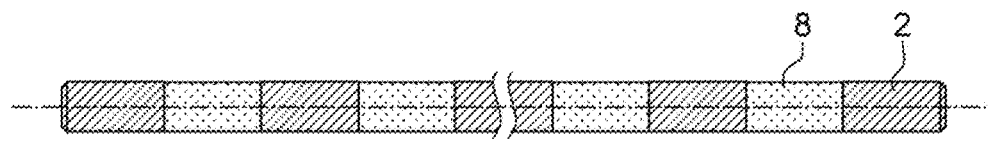
Figure 6C:
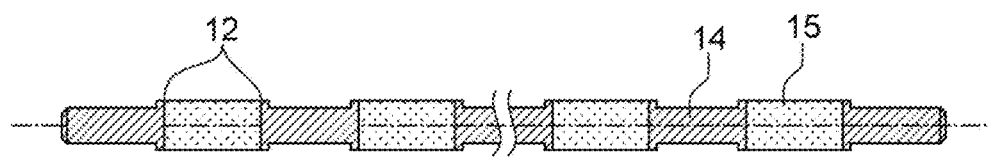
Figure 6D:
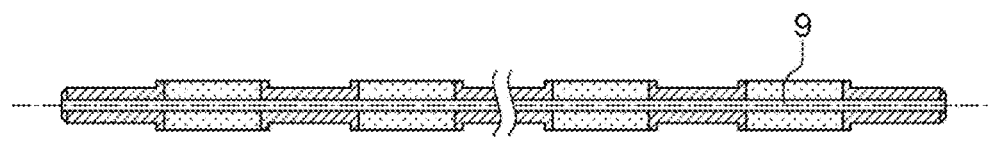
Figure 6E:
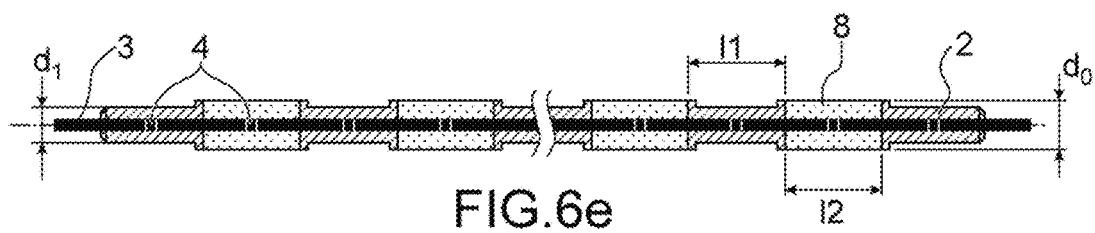

It should be noted that each of the assemblies depicted in FIGS. 1, 3 and 6e could be suitable for use in a metallic structure but that the assembly depicted in FIG. 1 could absolutely not be suitable for use in a reinforced concrete structure because of the absence of metallic shoulders.

1.1—Metallic Part

The metallic part 2 advantageously is in the form of a solid cylindrical bar with a circular cross section. More particularly, the metallic element is advantageously an iron or steel reinforcement, cylindrical in shape with a circular cross section, the diameter of which is between 5 and 16 mm. The metallic element may however have other forms and other cross sections (square, rectangular, hexagonal, etc).

Preferably, the length of the metallic element is of a metric or decametric order.

1.2—Optical Fibre

With regard to the choice of the optical fibre 3, it may be a monomode fibre, for example a fibre made from silica used in optical telecommunications (telecommunication standard, for example SMF-28 fibres), optionally sheathed, for example with epoxy-acrylate or polyimide, or even Ormocer (standing for "organically modified ceramics") depending on the polymerisation temperature of the thermosetting polymer used for compressing the fibre.

Where a monomode optical fibre is used, the signals recorded make it possible to obtain a deformation profile consisting of a corrosion profile and a thermomechanical profile (the global effect of temperature and axial deformation).

It is also possible to use "polarisation maintaining" fibres that have high birefringence obtained by manufacture (fibres of the PANDA type, with an elliptical or "bow tie" core). In this case, the signals recorded make it possible to obtain simultaneously the corrosion profile, the longitudinal deformation profile and the thermal profile of the metallic part on which the optical fibre is fixed. It is then possible to separate the temperature profile from the deformation profile by means of a second-degree matrix system as described by Frogatt et al. in "Distributing strain and temperature discrimination in unaltered polarization maintaining fibre", Optical Fibre Sensors Conference 2006, OFS 18, Cancun (reference [3]).

1.3—Transduction Means

The transduction means 4 can be formed by the optical fibre 3 itself. In this case, it is necessary for the resolution of the measuring and processing means used (in this case the OFDR technique) to be less than the length of the smaller portion among first and second portions, so that there is indeed at least one transduction means per portion, that is to say at least one measuring point per portion.

The transduction means 4 may also consist of Bragg gratings. In this case, it is necessary for there to be at least one Bragg grating per portion (whether it be the first portions 6 or the second portions 7), so that there is at least one transduction means per portion, that is to say at least one measuring point per portion.

A Bragg grating is a diffraction grating that is obtained by photo-inscription in the core of an optical fibre. A Bragg grating is in the form of a periodic pattern of index, which has a sub-micrometric pitch and a length of a few millimeters (typically 5 millimeters), and which reflects light at a particular wavelength (referred to as the Bragg wavelength).

1.4—Measuring and Processing Means

Figure 7:
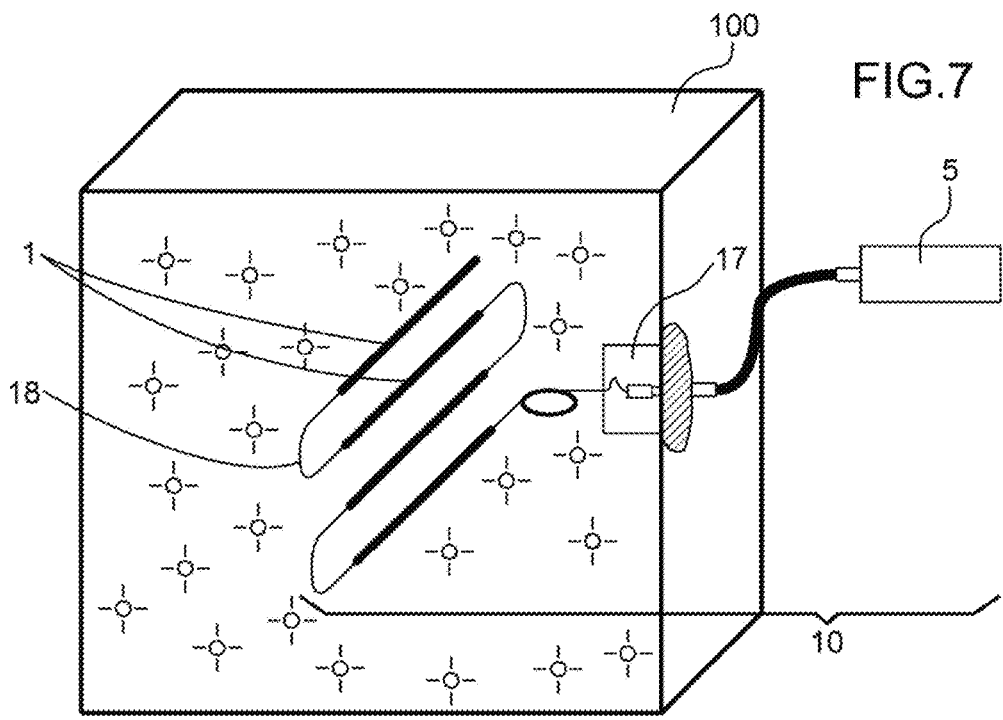
FIG. 7 depicts, schematically, an example of an installation of a device according to the invention in a civil engineering structure.

The measuring and processing means 5 are preferably offset outside the structure 100 to be monitored (FIG. 7).

Figure 8:
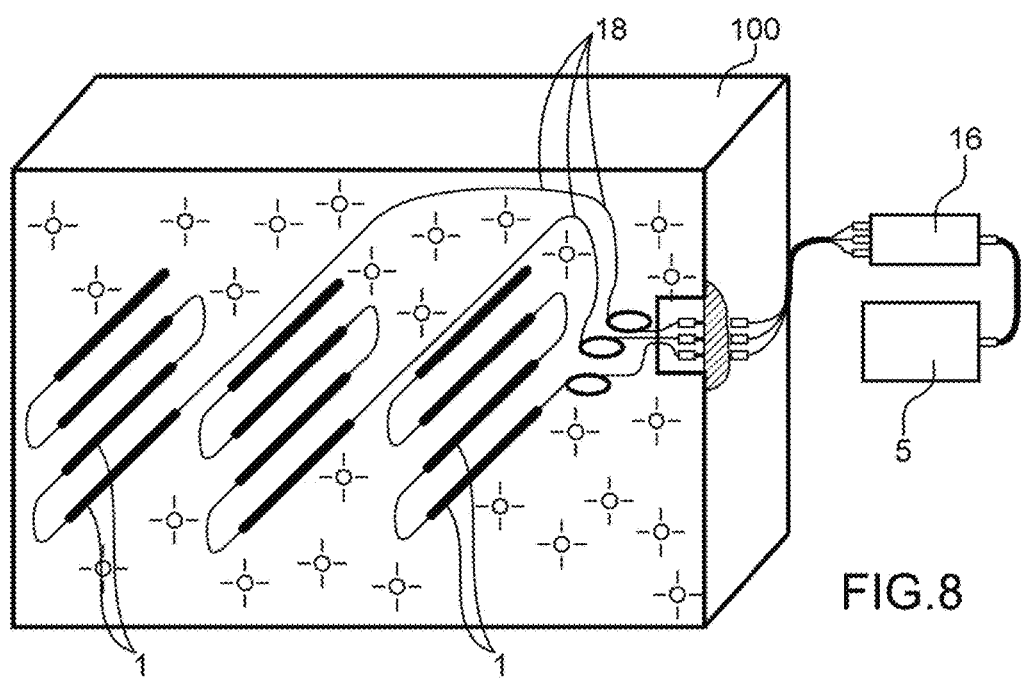
FIG. 8 depicts, schematically, another example of an installation of a device according to the invention in a civil engineering structure.

Preferably, the measuring and processing means 5 are mutualised and a single reading instrument is used to measure the data coming from each of the transduction means 4 of each optical fibre 3 of the assembly or assemblies 1 of the corrosion-measuring device 10 according to the invention (FIG. 8).

The measuring and processing means may be resident (that is to say permanently installed close to the structure 100 to be monitored) or roaming (that is to say moved from structure to structure when it is wished to perform corrosion measurements).

OFDR Method

When the transduction means 4 consist of the optical fibre 3 itself, the measuring and processing means 5 apply an OFDR (standing for "optical frequency domain reflectometry") technique.

The principle of the OFDR measuring technique is known (see for example the article by Froggat et al. "High-spatial resolution distributed strain measurement in optical fibre with Rayleigh scatter", *Applied Optics* 1998, 37(10), 1735-1740 (reference [4])) and is therefore not described here in detail. In a few words, the OFDR technique consists of injecting the light of a monomode laser, tuneable and emitting in continuous mode, into the core of an optical fibre (preferably monomode) and measuring the quantity of back-scattered (Rayleigh) light.

This OFDR technique makes it possible to address a continuum of measuring points all along the optical fibre, according to a centrimetric spatial resolution and with a range that is currently 70 meters (current limit of the reading instrumentation, improvable in the future), these points being identified in the spatial domain by a mathematical relationship of the inverse Fourier transform type.

Use of the OFDR technique requires performing two important operations on the optical fibre 3 before fixing it to the metallic part 2 in order to form an instrumented metallic part (assembly 1) for the measuring device 10 according to the invention.

Firstly, it is necessary to record a "native" OFDR backscatter profile of the optical fibre, before bonding.

Secondly, it is necessary to eliminate all significant backscatter sources liable to saturate the detector responsible for measuring the quantity of backscattered light. Thus the optical fibre is advantageously bias cleaved at the end in order to eliminate Fresnel reflection.

The location of the events on the metallic part is effected by means of the OFDR frequency profile determined from the calculation of intercorrelation between the native backscatter profile of the fibre and that of the assembly formed by the fibre bonded and prestressed on the metallic part. The prestressing deformation profile then reveals the prestressed region corresponding to the whole of the portion of fibre covered by—preferably embedded in—a thermosetting material (for example adhesive), when the prestressed state of the fibre is obtained by hot polymerisation.

The position in space of the front of this profile can then serve as a local reference in order to locate the measuring points along the metallic part 2 in a relative fashion, independently of the length of the offset between the transduction means 4 (location of the various measuring points) and the measuring and processing means 5 (reading instrumentation), which may change during the monitoring of the structure (modification to the optical cabling).

Bragg Method

When the transduction means 4 are Bragg gratings, the measuring and processing means comprise an opto-electronic measuring system for measuring the Bragg wavelength characteristic of each of the Bragg gratings.

The Bragg measuring method addresses a plurality of measuring points each covering a millimetric region, distributed at different regions chosen along the metallic part and often identified in the spatial domain by a distance/wavelength correspondence (spectral multiplexing).

For the record, an optical fibre provided with a Bragg grating and fixed to a metallic support forms a fibre optic sensor (FOS). The assembly 1 described in the present invention and comprising an optical fibre 3 provided with multiple Bragg gratings and fixed under prestressing on a metallic part 2 is equivalent to a multitude of FOSs connected in series. The operating principle of FOSs of the Bragg grating type is described in many publications (see for example the article by P. Ferdinand entitled "Bragg grating fibre optic sensors", *Techniques de l'ingénieur* 2001, R6735, 1-24 (reference [5])) and will therefore not be detailed here.

In a few words, the principle of the Bragg measuring technique consists of measuring the shift between this Bragg wavelength compared with a reference state, as a function of temperature or the local deformation state at the place of the Bragg grating being studied. For this purpose, a subtraction is made between the measured Bragg wavelength and the reference wavelength, measured during the calibration phase. It is a case fundamentally of a spectrometric measurement, insensitive to coupling disturbances (connection, optical transmission by the offset optical fibre connecting the optical fibre provided with Bragg gratings to the measuring means, etc), which makes this measuring method particularly robust on the field, under industrial conditions.

There exist several methods for reading Bragg wavelength, but it is preferred to use the best known and most widespread measuring method: a spectral measurement. This reading method uses a wide source emitting at around 1.55 µm, and a conventional spectrometer based on a diffraction grating or on a Fourier transformation method, which records the spectra of the Bragg gratings present on the optical fibre.

The precise determination of the wavelengths is usually obtained by a method of processing the signal of the half-height calculation type or by a mathematical adjustment to the response of the grating (for example the least squares (maximum likelihood) method).

As Bragg gratings are transducers multiplexible in the spectral domain, it is possible to place in series, and on the same optical fibre, a plurality of Bragg gratings with different wavelengths. The location of the Bragg gratings on the optical fibre (and consequently on the metallic part fixed to the optical fibre) is determined by their wavelength. The location of the events on the metallic part is therefore determined by a correspondence between the wavelength and the position (spectral multiplexing).

By way of example, let us consider the case where the Bragg gratings are subjected to the same temperature (which corresponds to an insertion in a large civil engineering structure) and subjected to a range of deformations of approximately one thousand microdeformations (which corresponds to the typical conditions applied to reinforcements or to extensometers with a steel test body). The corresponding wavelength range is 1.2 nm per Bragg grating (the conversion coefficient is equal to 1.2 pm ($1.2 \times 10^{-12}$ m) per microdeformation for a source at 1.55 µm). As the spectral extent of the source may be as much as 80 nm (extended telecom band known as "C+L"), the number of Bragg gratings that can be multiplexed on a single optical fibre can therefore be as much as 60 to 70 per metallic part.

By way of examples, such a capacity of 70 Bragg gratings (that is to say 35 segmentation patterns) would make it possible to achieve a total length of instrumented metallic part of 140 cm, in the case of a period of 40 mm and a segmentation pattern of 18/40, or 3.5 meters in the case of a period of 100 mm and a segmentation pattern of 80/100.

Figure 5A:
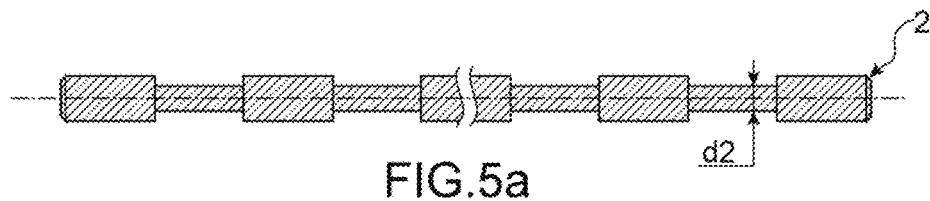
FIGS. 5a to 5c depict steps of the method for producing an assembly of the device according to the invention, according to a particular embodiment.
Figure 5B:
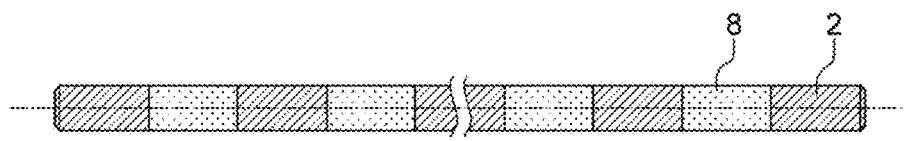
Figure 5C:

2—Example Embodiments Of A Metallic Part Instrumented By An Optical Fibre Provided With Transduction Means For A Corrosion Measurement Device According To The Invention A first example embodiment is described in FIGS. 5a to 5c and makes it possible to obtain the assembly depicted in FIG. 3.

In this example embodiment, the metallic piece 2 is obtained by working from a block of material that is in the form of a metallic rod with a circular cross section having a diameter $d_0$, for example a reinforcement.

First of all, the metallic rod is cast, machined or forged, for example by stamping, in order to form cylindrical segments with a diameter $d_2$ less than the initial diameter $d_0$ (FIG. 5a).

Then the metallic part 2 thus obtained is coated with a corrosion-protection material over its entire length, to the diameter $d_0$, in order to form a layer 8 (FIG. 5b).

Finally, the metallic part 2 is grooved over its entire length by milling or rebating and an optical fibre 3 is placed in the groove, the fibre being in a prestressed state under compression (FIG. 5c).

It should be noted that, unlike the assemblies depicted in FIGS. 1 and 3, the assembly illustrated in FIG. 5c is depicted in plan view, which makes it possible to observe the fibre housed in the groove.

More details on the way of effecting the machining of the metallic part, the materials to be used, etc., are available in the following description of the second example embodiment. These details can of course also be used for the first example embodiment.

The second method example is broken down into five main steps, illustrated in FIGS. 6a to 6e:

first turning of a block of metallic material (FIG. 6*a*);
deposition of a coating resin by pultrusion method or electrostatic powder coating (FIG. 6*b*);
second turning of the block of material (FIG. 6*c*);
grooving over the entire length of the block of material (FIG. 6*d*);
placing of the fibre at the bottom of the groove, application of an adhesive (for example an epoxy resin or a cyanoacrylate adhesive) and hot polymerisation (FIG. 6*e*).

As in the first example embodiment, the metallic part 2 is obtained by working from a block of material in the form of a metallic rod with a circular cross section, for example a reinforcement.

During a first step, a block of material is cast, machined or forged, for example by stamping, advantageously periodically over its entire length, in order to form a metallic part 2 having cylindrical segments with a diameter $d_2$ less than the initial diameter $d_0$ of the metallic part (FIG. 6*a*). This is however in no way limitative: the segments of diameter $d_0$ and the segments of diameter $d_2$ follow each other in alternation, but are not necessarily periodic and may have different lengths.

In the context of this second example embodiment, we adopt the particular case of a periodic pattern: the lengths of the segments uncovered 14 and covered 15 are called $I_1$ and $I_2$ respectively and L is the period of the segmented pattern where $L=I_1+I_2$.

The segmentation pattern is defined as the proportion of uncovered length:

$$M = \frac{I_1}{L}$$

By way of example, this segmentation pattern has a period of 40 mm, and the values of $I_1$ and $I_2$ are respectively equal to 18 mm and 22 mm. The value of the segmentation pattern is therefore close to 0.5 (18/40). This example is however in no way limitative and a different value may also be preferred. For example, when the transduction means are Bragg gratings, it is particularly advantageous to choose a value close to 0.8 or 0.9, in order to increase the range of the measurement.

Preferably, a value of $I_2$ close to 2 cm and a value of $I_1$ adjustable between 2 cm and 20 cm will be chosen (so as to obtain a pattern M of between 0.5 and 0.9 approximately.

Still by way of example, the metallic part 2 has an initial diameter $d_0=10$ mm and a reduced diameter $d_2=6$ mm.

During a second step, the metallic part is coated with a corrosion-protection material over its entire length, to the diameter $d_0$, in order to form a layer 8 (FIG. 6*b*).

Various materials can be used to form the layer 8, and in particular thermosetting polymers; it is however advantageous to use polymer materials resistant to bases (pH greater than 13), at high temperatures (above 120° C.), and having low absorption of moisture.

The hard polymer for forming the layer 8 can thus be chosen from thermosetting resins such as polymers, which are widely used for producing boats, swimming pools or tanks. It may also be chosen from vinyl ester resins, which are advantageous because of their corrosion resistance. Finally, epoxy resins can also be used, but are more expensive.

In order to proceed with the coating of the metallic part, it is possible to use a pultruding machine (pultruder). For the record, a pultruder comprises a polymer injector, a preformer adapted to the form of the part (here a bore with a diameter $d_0=10$ mm), and an induction furnace locally heating the metallic part and polymerising the deposited material. The metallic part is drawn through the pultruder so that the thermosetting polymer can be injected into the machined parts of the metallic part.

In order to proceed with the coating of the metallic part, it is also possible to place it on a conveyor and to pass it through an electrostatic powder-coating bench (an electrostatic powder-coating bench being composed of a surface-preparation (by shot blasting) section, an induction furnace, a tunnel for applying the thermosetting polymer, in the form of powder, by electrostatic powder coating, and finally a cooling area). The crosslinking of the powder occurs as soon as it reaches the preheated metallic part. In this case, the thermosetting polymer is usually an epoxy resin, optionally coated with a layer of high-density polyethylene (PEHD), PEHD being suited to saline and basic environments.

During a third step, the metallic part thus coated is once again turned on the segments left uncovered over a diameter $d_1$ (that is to say 9 mm in the example illustrated): the uncovered segments 14 of diameter $d_1$ are obtained.

Preferably care is taken to leave a shoulder 12 on each side (for example with a height of 0.5 mm) (FIG. 6*c*).

During a fourth step, the metallic part is grooved over its entire length by milling or rebating (FIG. 6*d*). In our example embodiment, we have chosen to produce a groove 9 that is 1.5 mm deep and 1 mm wide, but other choices of values are possible.

During a fifth step, an optical fibre 3 is placed in the groove and is held non-tensioned at the bottom of the groove, for example by means of spots of adhesive or a fixing paste.

The metallic part provided with the fixed fibre is then inserted in a tubular furnace (for example an inductive furnace), which raises its temperature to between 80° C. and 140° C. (the choice of the temperature being made according to the type of material that it is wished to deposit on the optical fibre in order to stress it under compression). The metallic part is placed in translation, at a speed compatible with the temperature rise time of the metallic part and the duration of polymerisation of the material that it is wished to deposit on the optical fibre (a few minutes per meter).

As a material for stressing the optical fibre under compression on the metallic part, a thermosetting material can be chosen.

Immediately on emerging from the furnace, the thermosetting material is injected into the groove, preferably up to the top, in order to provide future mechanical contact between the material of the metallic part and the material of the body of the structure to be monitored (for example a mechanical contact between steel and concrete when the metallic part is made from steel and the structure to be monitored is made from concrete). It is possible for example to use an injection nozzle that delivers a continuous flow, suited to the translation speed of the metallic part.

As soon as the thermosetting material comes into contact with the heated metallic part, the thermosetting material passes through a state of great fluidity that enables it to fill in the space between the metallic part and the fibre and to form a layer 11 around the optical fibre, just before polymerising at high temperature, on emerging from the furnace.

Finally, the metallic part gradually cools as it is discharged out of the furnace and the optical fibre is then prestressed under compression because of the great difference in coefficient of expansion between the metallic part and the fibre ($\alpha_{steel} \approx 12 \cdot 10^{-6}$/K and $\alpha_{SiO2} \approx 0.5 \times 10^{-6}$/K) (FIG. 6e).

By way of example, the thermosetting material used to form the layer 11 can be chosen from epoxy resins polymerising at high temperature (between 80° C. and 140° C.) and withstanding well an environment at a high pH such as the one existing in concrete.

Finally, in order to produce the assembly depicted in FIG. 1, it is possible for example to use a metallic part with a constant diameter, on which rings of corrosion-protection material will be extruded, spaced apart from one another. Then a groove is produced in these rings, an optical fibre is placed in the groove and a thermosetting material is injected onto the fibre so that it is coated with this material, whether the fibre is in the groove (FIG. 2b) or in the portions situated between the rings (FIG. 2c). This thermosetting material will thus have the function of compressing the fibre in a pre-stressed state and protecting it from any slight mechanical shocks that it might suffer.

It should be noted that, in the assemblies illustrated in FIGS. 1 and 3, there is only one optical fibre and only one groove 9, but it would be entirely possible to have assemblies having several optical fibres and several grooves, oriented along the longitudinal direction of the metallic part.

In the device according to the invention, and as illustrated in the above examples, it is found that, because of the segmentation, the optical fibre 3 is alternately secured to a corrosion-protection material forming the layer 8—in the portions of the metallic part protected against corrosion (first portions)—and secured to the metal of the metallic part 2—in the portions of the metallic part not covered with the corrosion-protection material (second portions).

This segmentation makes it possible to achieve two objectives, which are as follows:

firstly, the corrosion agents (chlorides, sulfates, $CO_2$) interact selectively on the metal segments not covered by the corrosion-protection material (uncovered segments 14 in FIG. 6c) (at least initially in the corrosion propagation, before it propagates under the covered segments 15);

secondly, the alternation of covered segments and uncovered segments (segments 15 and 14 in FIG. 6c) make it possible to distinguish the two mechanical contributions in the spatial domain, namely that due to the thermomechanical action and that due to corrosion. This is because the thermomechanical action extends over the whole of the metallic part (covered and uncovered segments), since it is mechanically fixed to the structure. Moreover, as the temperature gradients are low within a structure of large size and high inertia, the temperature may be considered to be constant between two successive segments of centimetric length. As for the corrosion action, it is located on the uncovered segments.

It is important that in the covered segments (the first portions of the metallic part covered by the corrosion-protection material), the optical fibre is never in direct contact with the metallic part since it could constitute a point for progression of the corrosion. However, if there is corrosion of the metallic part, it is necessary that it should occur first of all in the uncovered segments rather than in the covered segments. This is the reason why it is preferable for the depth of the groove to be chosen so as to be less than the thickness of the layer of corrosion-protection material, this situation being the most favourable since it guarantees good impermeability vis-à-vis corrosion products, whatever the method undertaken for bonding the fibre in the groove. It is possible to produce deeper grooves than the thickness of the layer of corrosion-protection material but, in this case, the impermeability must be provided by the film of adhesive, which cannot be a sufficient guarantee of sealing (the case of an imperfect film of adhesive with gaps for example).

In the examples illustrated in FIGS. 5a to 5c and 6a to 6e, the choice of the diameters $d_0$ (if it is wished to form shoulders), $d_1$ and $d_2$ is made with the following relationships taken into account:

$$d_0 > d_1 > d_2$$

$$r < (d_1 - d_2)/2$$

where r is the depth of the groove with respect to the metal surface of diameter $d_1$.

Thus this guarantees that there is always a thickness of corrosion-protection material between the optical fibre and the metallic part in the covered segments, even in the case where the fibre is situated at the bottom of the groove.

3—Example of a Procedure for Installing a Corrosion Measuring Device According to the Invention in a Civil Engineering Structure Made from Reinforced Concrete The measuring device 10 as illustrated in FIG. 7 comprises four assemblies 1 (four instrumented metallic parts), connected in series, and a measuring unit, grouping together the measuring and processing means 5 of the transduction means of the instrumented parts and a light source (not shown), the four assemblies 1 being embedded in the structure 100 (here a civil engineering structure) and the measuring unit comprising the measuring and processing means 5 being placed outside the structure, an optical interface connecting the end of one of the instrumented metallic parts to the measuring unit.

In this example embodiment, the four assemblies 1 are placed in series and connected by a reinforced optical fibre cable (for example an aramid braid), this cable being connected to a single-channel sealed optical feedthrough.

Depending on whether the transduction means are an optical fibre or a Bragg grating, the measuring unit comprises a spectrometer or an OFDR reflectometer.

It is important for the optical interface situated at the surface of the structure to remain fluidtight in order not to constitute a point of entry inside the structure for corrosive substances and moisture. For this purpose, a housing 17 can be formed by formwork inside the wall of the structure 100 (as depicted in FIGS. 7 and 8) in order to protect the optical connection, and a sealed optical feedthrough used for connecting the optical connections to the measuring unit.

It should be noted that in practice passive reinforcements, used for mechanically reinforcing a concrete structure, are assembled in a lattice. However, for reasons of clarity, only the passive reinforcements instrumented by optical fibre (that is to say the four instrumented metallic parts of the device according to the invention) are represented in FIGS. 7 and 8.

The mounting of the instrumented metallic parts of the structure is left to the choice of the operator.

By way of example, the operator may choose to place several instrumented metallic parts in series at a constant depth over the entire length of a large structure, in order to cover a surface area that is as wide as possible. This is what is illustrated in FIG. 7, where four instrumented reinforcements are assembled in series by means of an optical cable 18 in a vertical plane, parallel to the wall of the structure.

However, other mountings of instrumented metallic parts in the structure are also possible. The operator may for example choose to place several networks of instrumented metallic parts such as those illustrated in FIG. 8. In FIG. 8, there are several assemblies similar to those illustrated in FIG. 7 that are connected in parallel by means of a multi-channel sealed optical feedthrough. The instrumented reinforcements are thus assembled in several planes parallel to the wall of the structure, and at different depths. This configuration makes it possible to monitor the advance of a corrosion front, for example a carbonation front.

As illustrated in FIG. 8, it is found that it is entirely possible, for economic reasons, to use a single measuring unit 5, similar to that depicted in FIG. 7. In this case, an optical switch 16 makes it possible to connect all the channels to the measuring unit in a parallel addressing mode. In fact, the measurement is not made simultaneously on all the channels but sequentially, one channel after the other.

In practice, the signals are averaged over a large number of acquisitions in order to reduce the statistical uncertainty. Thus the measuring time is around a few minutes per channel, that is to say around one hour for a sealed optical feedthrough of 16 channels. Nevertheless, this is in no way limitative since the thermomechanical development of a civil engineering structure has comparable kinetics.

Finally, it should be noted that the assemblies that are illustrated in FIGS. 7 and 8 may entirely be reproduced in several examples for the same structure, in order to increase the number of instrumented metallic parts.

4—Separation of Deformations Due to Thermomechanical Stresses from Those Due to Corrosion A description will now be given on how to analyse the results obtained by each of the instrumented metallic parts of the device according to the invention, and more precisely how to effect the separation of the wavelength (or frequency) shifts due to thermomechanical stresses from those due to corrosion.

When one or more instrumented metallic parts of a device according to the invention are mounted on the surface or inside a structure, for example a concrete structure, the instrumented metallic part or parts are mounted so as to be mechanically fixed to the structure and are therefore not only sensitive to corrosion but also to the thermomechanical disturbances related to the loading of the structure, as well as to the temperature cycles that it experiences.

Thus, as with the FOSs described in the prior art, it is necessary to separate the contributions caused by corrosion from those caused by the thermomechanical contributions of the structure, in order to be able to use the instrumented metallic part or parts in a real situation. This is because the range of deformations of thermomechanical origin of a metallic structure or one comprising at least one metallic reinforcement may be as much as approximately 500 micro-deformations, or even more, and therefore exceed the range of deformations caused by the corrosion phenomenon.

For this purpose, it is necessary to first produce a reading of wavelengths (or frequencies) for each of the instrumented metallic parts of the device as soon as the structure to be monitored is brought into service in order to obtain a reference profile ("zero state"), in the absence of corrosion.

Then, periodically over time, profiles are recorded at the same time in order to compare them with the reference profile so as to monitor the appearance of corrosion and, where applicable, to locate it precisely on a metallic part of one or more instrumented metallic parts and to determine the magnitude thereof.

When the Bragg method is used, the thermomechanical profile is deduced from the spectral shifts between the reference Bragg wavelengths and those measured at each of the measuring points (where the Bragg gratings are situated) on the first portions (the proportions of the metallic part protected from corrosion).

When the OFDR method is used, the thermomechanical profile is deduced from the calculation of autocorrelation between the native backscatter profile of the optical fibre and that of the instrumented metallic part on the first portions to which said optical fibre belongs.

In a reinforced concrete civil engineering structure, the temperature gradients are low (a few tenths of degrees per centimeter), so that the thermomechanical base line can be considered to be identical on two adjacent portions separated by a few centimeters (which is the case in our example embodiment). In practice, a conventional monomode fibre therefore suffices to distinguish the corrosion effects from the thermomechanical effects. In the particular case where the temperature gradient is higher, a polarisation-maintaining multimode fibre could be used in replacement for a conventional monomode fibre, for the purpose of distinguishing the temperature profile from the deformation profile using the previously described procedure.

Likewise, deformation gradients are of small magnitude in a sound structure. On the other hand, in a cracked structure, most of the force is then absorbed by the instrumented metallic part at the location of the crack, then revealing a localised increase in the deformation profile. Analysis of the deformation profile does however make it possible to discern the appearance of a corrosion crack, as testified to by FIG. 9.

4.1—Calibration of the Instrumented Metallic Parts

In order to be able to distinguish the stresses, the first step is to effect the calibration of each of the instrumented metallic parts of the device that is the subject matter of the invention.

At least one reference thermomechanical profile ("base line") is first of all recorded as soon as the structure is brought into service for the first and second portions of each of the instrumented metallic parts of the device.

This reference thermomechanical profile is normally recorded at a very precise time in order to have a thermomechanical condition that is as stable and reproducible as possible, typically between 5 a.m. and 6 a.m. when the structure has thermalised throughout the night and before a new temperature gradient caused by solar illumination appears.

The covered segments (corresponding to the first portions) have lower rigidity than the uncovered segments (corresponding to the second portions), because of their difference in metallic cross section in the example embodiments depicted in FIGS. 4a, 5c and 6e. The rigidity corresponds to the product of the Young's modulus and the cross section. The equilibrium of the forces inside the structure therefore results in two distinct deformation profiles for each type of segment, the deformations observed on the covered segments being greater than the deformations measured on the uncovered segments (with a greater metallic cross section).

The calibration consists of determining the experimental ratio between the two deformations measured on two consecutive segments of the same segmentation pattern. As a first approximation, this ratio Q depends on the quotient of the squares of the diameters of the metallic cross sections of the two segments.

In the examples described above where $d_1=9$ mm and $d_2=6$ mm have been chosen, $Q = (d_2/d_1)^2 \approx 2.25$.

4.2—Measurement of Corrosion

In a global or localised corrosion situation, the deformation profile contains a contribution of additional deformation in the uncovered segments, absent in the covered segments (at least when the corrosion first appears).

An example of a mathematical procedure for measuring corrosion consists of mathematically adjusting the thermomechanical profile ("base line") from the values of deformations $\epsilon_c$ measured in the covered segments (protected from corrosion). This mathematical adjustment over a plurality of measuring points reduces the variance compared with a measurement at a single point and therefore improves the final precision. An interpolation of this base line is then effected (on all the uncovered segments) by adjustment of the type consisting of a least squares analysis of a polynomial function the degree of which is reduced to 2 or 3 in order to reduce the risks of oscillations.

These procedures exist routinely in many data acquisition software packages.

The interpolated values are then weighted by the calibration coefficient Q, determined during the calibration of the instrumented metallic parts of the device that is the subject matter of the invention, in order to derive therefrom the equivalent deformation on an uncovered segment.

A subtraction is then made between the deformation values measured on the uncovered segments and the reconstituted base line (on the uncovered segments) in order to reveal the contribution of deformation solely due to corrosion.

For each of the segmentation patterns, the following calculation is then made:

$$\Delta\epsilon = \epsilon_u - Q \cdot \epsilon_c$$

where $\epsilon_u$ and $\epsilon_c$ are the deformations measured on the uncovered and covered segments respectively, and $\Delta\epsilon$ is the deformation differential that can be ascribed to corrosion.

4.3—Measurement of the Thermomechanical Contribution of the Structure

The deformation profile obtained from the covered segments directly gives access to the distribution of the thermomechanical forces along each instrumented metallic part.

Furthermore, as the instrumented metallic part is mechanically fixed to the structure (for example, when it is embedded in the concrete as a reinforcement or when it is fixed (for example by means of screws) to a metallic structure (the hull of a boat, for example)), it also behaves as an extensometer. It therefore makes it possible to measure the distribution of the deformations along the metallic piece and thus gives a global indication of the loading of the structure during its life cycle.

If a conventional optical fibre is used, the operator has access to the thermomechanical profile (equivalent deformation that is a function of the temperature and deformation effects).

If a polarisation-maintaining optical fibre is used, the operator can have access to the temperature deformation profiles, via the inversion of a matrix system.

Where the structure is a reinforced concrete structure, the instrumented metallic part also makes it possible to locate any cracks in cases where the concrete is locally under excessive traction beyond 150 to 200 microdeformations). As already seen above, the appearance of a localised crack in the structure results in a local increase in the deformation since the loading at the point of the crack is entirely absorbed by the instrumented metallic part. As the amplitude of the deformation caused by a crack is different from that caused by corrosion, it is possible to distinguish the two.

5—Identification of the Corrosion Process

Once the corrosion has been detected, it must be possible to identify the corrosion process.

As a reminder, several corrosion processes are liable to appear in the environment of the structure.

When the structure is made from reinforced concrete, the corrosion processes are as follows.

In coastal regions or ones that are frequently under snow (requiring the use of de-icing salts), the chlorides issuing from the salt water diffuse in the concrete, and can destroy the layer of protective oxide situated around the reinforcements and penetrate the steel. A localised corrosion process by pitting can then start, accelerated by the increase in conductivity of the aqueous electrolyte. The iron then degrades into green rust which dissolves and repreciptates in the form of rust (iron oxide). The precursor corrosion products (green rusts) are in the form of gels, with low mechanical rigidity, and can be discharged by the open cracks present in the structure.

A second corrosion process is related to the carbonation of concrete. As time passes, the carbon dioxide ($CO_2$) present in the air migrates into the thickness of the material of the structure and reacts with the material (Portlandite) in order to form calcium carbonate ($CaCO_3$), causing a reduction in the pH of the interstitial solution (to approximately 8 to 9). The carbonation front then progresses in the coating of the concrete over a depth of several centimeters. When the carbonation front reaches the reinforcement, depassivation of the reinforcement occurs, which gives rise to a generalised corrosion process causing the formation of iron oxy-hydroxides (FeOOH) occupying a higher volume than the initial iron (between 3 and 6 times more).

Unlike attacks by chlorides, the carbonation corrosion products have a Young's modulus close to that of steel ($\approx 100$ GPa) so that the corrosion is accompanied by a compression of the iron/concrete interface resulting from the increase in volume occupied by the oxidised residues. The result is a cracking of the concrete cover and a reduction in the cross section of the reinforcements and of the steel/concrete adhesion (spalling), thus reducing the life of the structure.

Finally, a third corrosion process corresponds to the sulfation of the steels related to an attack by acids contained in sea water or gypsum-containing water (rich in selenite or lime sulfate). Just as with carbonation, it also results in a spalling of the concrete cover.

When an instrumented metallic part is embedded in a concrete structure and is subjected to one of the two typical corrosion mechanisms (pitting or sulfation/carbonation), the sign of the development of the stress applied makes it possible to deduce whether it is essentially a case of an attack by chlorides or by sulfation/carbonation. The same instrumented metallic part therefore makes it possible to distinguish the essential corrosion mechanisms.

In the case of corrosion by chlorides, the corrosion residues have lower cohesion and rigidity (pitting). The layer covering the optical fibre and serving to keep it in a prestressed state under compression (for example a layer of thermoset material such as a film of adhesive) is detached from the metallic part, helping to release the compression prestressing applied to the optical fibre (in other words, the optical fibre returns towards its initial state, before application of the prestress). An apparent traction of the optical fibre is then observed, with an amplitude equivalent to the compression prestressing but of the opposite sign, that is to say typically +1200 microdeformations.

In the case of corrosion by carbonation (low pH, around 8 to 8.5), the corrosion residues of the metallic part have a high volume and rigidity equivalent to that of the non-corroded part (for example 200 GPa for a metallic part made from steel). The corrosion results in the formation of a film of oxide on the metallic part (iron oxide on the metallic part if this is made from steel) and, as this film of oxide keeps its cohesion, the result is a compression of the pair formed by the instrumented metallic part and the concrete structure with equilibrium of the stresses. This compression of the hydrostatic type is added to the compression prestressing of the optical fibre. Since the concrete is a less rigid material than steel ($E_{concrete} \approx 30$ GPa), the latter deforms approximately 7 times more. As the concrete cover ruptures ($\approx 200$ microdeformations), the pressure reached is around 6 to 10 MPa (i.e. between 60 and 100 bar). The magnitude of the equivalent deformation is around a few tens of microdeformations (between −30 and −50 microdeformations). The amplitude is therefore much lower than in the case of corrosion by chlorides but does however remain observable with Bragg or OFDR optical instrumentations, which have a resolution of a few microdeformations.

In a combined corrosion situation, the effect of the chlorides is preponderant since it gives rise to a greater change in wavelength related to the mechanical degradation of the metallic substrate.

Finally, where the instrumented metallic part passes through a crack in the structure, the deformation trace reveals a localised increase that cannot however be confused with the manifestation of corrosion since its expected amplitude is different from that obtained by corrosion.

Figure 9:
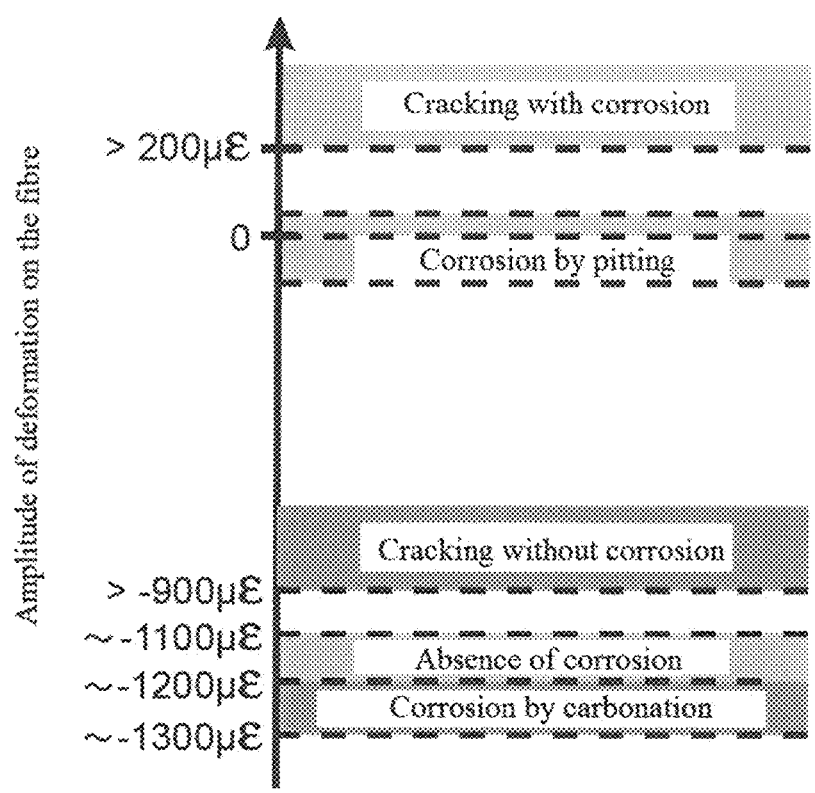
FIG. 9 is a specimen diagram illustrating a corrosion and/or crack diagnosis in a reinforced-concrete structure according to ranges of values of the amplitude of deformations measured in an optical fibre.

All these results are compiled in FIG. 9, which gives the distribution of the corrosion risks by deformation zone (the risk zones being distinguished in terms of deformation amplitude). This diagram shows that the processes involved in a civil engineering structure made from reinforced concrete can be distinguished in terms of deformation amplitude for the purpose of providing a diagnosis on the good health of the structure.

It should be noted that, when the structure is metallic, only pitting corrosion can be measured by the device according to the invention.

6—Examples of Application of the Device According to the Invention

As seen previously, one or more instrumented metallic parts of the device that is the subject matter of the invention can be used as a passive reinforcement (reinforcement rod) in a civil engineering structure made from reinforced concrete, and at the same time provide diagnosis on the state of corrosion of the passive reinforcements embedded inside the structure.

After processing of the signal on the deformation data according to the procedure described above, an instrumented part of the device that is the subject matter of the invention makes it possible to estimate the corrosion profile over the entire length of the instrumented metallic part by means of one or more optical fibres and thus to provide early and precise detection of the corrosion in a structure.

Whatever the meteorological method used (Bragg or OFDR), the operator can then locate the appearance of the corrosion, identify the essential diagram of the corrosion reaction (expansion or pitting) and follow its progress over time in correlation with the climatic events and the loading of the structure.

The operator thus has an innovative and original operational tool making it possible to envisage the establishment of condition-based maintenance (CBM), with a view to reducing the costs of inspecting structures and improving the intervention and restoration strategy.

The instrumented metallic parts also make it possible to achieve high coverage, by increasing the number of instrumented metallic parts that the measuring device according to the invention has.

The device according to the invention also makes it possible to achieve an in situ and in-depth diagnosis in a structure, as well as its foundations, areas inaccessible to observation.

The structures concerned are tunnels, buildings, bridges, dams, cooling towers and nuclear power stations, offshore structures, marine turbines, wind turbines and foundations of coastal or marine structures (dykes, jetties, etc.), underground structures, etc.

Finally, other examples of applications are possible, such as for example the measurement of corrosion in metallic structures, for example transport structures such as aircraft and boats. In this case, the instrumented metallic part or parts of the device that is the subject matter of the invention are intended to be fixed on the surface of a structure or used simultaneously as a reinforcement element (for example as a spar, tendons, etc.) and as a corrosion telltale, in order to precisely detect and locate corrosive attacks.

REFERENCES CITED

[1] S. K. T. Grattan et al.
Monitoring of corrosion in structural reinforcing bars: performance comparison using in situ fiber-optic and electric wire strain gauge systems, *IEEE Sensors Journal* 2009, 9(11), 1494-1502

[2] J-R. Lee et al.
A structural corrosion-monitoring sensor based on a pair of prestrained fiber Bragg gratings, *Measurement Science and Technology* 2010, 21(1), 017002.1-017002.7

[3] M. Froggatt et al.
Distributing strain and temperature discrimination in unaltered polarization maintaining fiber, *Optical Fiber Sensors Conference* 2006, OFS 18, Cancun

[4] M. Froggatt et al.
High-spatial resolution distributed strain measurement in optical fiber with Rayleigh scatter, *Applied Optics* 1998, 37(10), 1735-1740

[5] P. Ferdinand
Bragg-grating optical fibre sensors, *Techniques de l'ingénieur* 2001, R6735, 1-24

What is claimed is:

1. Device for measuring corrosion in a metallic structure or in a structure comprising at least one metallic reinforcement, said device comprising:
   at least one assembly that comprises:
   a metallic solid part configured to be mechanically secured to the structure, the metallic solid part extending in a longitudinal direction between two ends and having a lateral external surface which connects the two ends, the metallic solid part being able to undergo stresses under the effect of corrosion and/or a thermomechanical variation; and
   transduction means comprising an optical fibre, the optical fibre being fixed on the lateral external surface of the metallic solid part in a prestressed state under compression so as to undergo stresses suffered by the metallic solid part, the transduction means being able to modify light propagating in the optical fibre under effect of stresses applied to the optical fibre, thereby providing varying spectral responses; and measurement and processing means for measuring and processing the spectral responses supplied by the transduction means of said at least one assembly, wherein the lateral external surface of the metallic solid part of the at least one assembly is partially covered with a layer of corrosion-protection material, thereby obtaining an alternation of first and second portions of the metallic solid part, arranged in the longitudinal direction of the metallic solid part, wherein the first portions are covered with the layer of corrosion-protection material while the second portions are not covered with the layer of corrosion-protection material, wherein there is at least one of the transduction means in each of the first and second portions, so that the transduction means associated with the first portions supply first spectral responses that translate application of a thermomechanical stress to the first portions, while the transduction means associated with the second portions supply second spectral responses that translate application of a thermomechanical stress and/or a corrosion to the second portions, and wherein the layer of corrosion-protection material comprises a groove in which the optical fibre is housed; and wherein the measurement and processing means further comprise means for comparing the first spectral responses supplied by the transduction means associated with the first portions and the second spectral responses supplied by the transduction means associated with the second portions, thereby establishing a corrosion profile of the metallic solid part.

2. Measuring device according to claim 1, wherein, for at least one assembly, the groove in which the optical fibre is housed is formed in the lateral external surface of the metallic solid part, thereby being present in the second portions of the metallic solid part.

3. Measuring device according to claim 1, wherein, for at least one assembly, amongst the first and second portions of the metallic solid part, first and second portions which are adjacent form a periodic pattern that is repeated in the longitudinal direction of the metallic solid part.

4. Measuring device according to claim 1, wherein, for at least one assembly, a layer made from a thermoset material covers the optical fibre and compresses the optical fibre on the metallic solid part, thereby the optical fibre is configured in a prestressed state under compression.

5. Measuring device according to claim 1, wherein, for at least one assembly, the metallic solid part of each assembly of the device comprises shoulders arranged in the longitudinal direction of the metallic solid part.

6. Measuring device according to claim 1, wherein, when the structure is metallic, the metallic solid part of each assembly is made from a material that is similar, preferably identical, to the material of the structure and, when the structure is not metallic and comprises a metallic reinforcement, the metallic solid part of each assembly is made from a material that is similar, preferably identical, to the material of the metallic reinforcement.

7. Measuring device according to claim 1, wherein, for at least one assembly, the transduction means are formed by an optical fibre or Bragg gratings photoinscribed in an optical fibre.

8. Measuring device according to claim 7, wherein, when the transduction means are formed by Bragg gratings photoinscribed in an optical fibre fixed to a metallic solid part, each of the first and second portions of this metallic solid part is associated with at least one Bragg grating and the measuring and processing means comprise an optoelectronic measuring system for measuring Bragg wavelength characteristic of each of Bragg gratings photoinscribed in the optical fibre.

9. Measuring device according to claim 7, wherein, when the transduction means consist of an optical fibre, the measuring and processing means apply a technique of measuring by OFDR Rayleigh reflectometry to this optical fibre, measuring resolution of this technique being chosen so as to be centimetric and less than the smallest of the first and second portions of the metallic solid part on which the optical fibre is fixed.

10. Measuring device according to claim 1, comprising several assemblies, said assemblies being connected in parallel and/or in series.

11. A method for detecting corrosion in a structure comprising a main body, that is metallic or that is made from concrete and one or more metal reinforcements, wherein the method comprises:

providing a device according to claim 1, at least one of the metal reinforcements of the structure consisting of the metallic solid part of an assembly of the device, the metallic solid part having an alternation of first and second portions; and measuring and processing spectral responses supplied by transduction means of the assembly of the device; and comparing the spectral responses supplied by the transduction means associated with the first portions of the assembly and those supplied by the transduction means associated with the second portions of the assembly, in order to establish a corrosion profile of the metallic solid part, thereby detecting corrosion in the structure.

12. A method for providing a corrosion telltale for a metallic structure, wherein the method comprises:

providing a device according to claim 1, the metallic solid part having an alternation of first and second portions; and fixing the metallic solid part of each assembly of the device to the surface of the structure; and measuring and processing spectral responses supplied by transduction means of each assembly of the device; and comparing the spectral responses supplied by the transduction means associated with the first portions of each assembly and those supplied by the transduction means associated with the second portions of each assembly, in order to establish a corrosion profile of the metallic solid part, thereby providing a corrosion telltale for the metallic structure.

13. A method for detecting and locating the corrosion on a metal solid part of an assembly of the device as defined in claim 1, the metal solid part being mechanically secured to a metallic structure or a structure comprising at least one metallic reinforcement, the method comprising, for each assembly, the following steps:

measuring a change in amplitude of the spectral response over time for each of the first and second portions of the metallic solid part;

determining a contribution of the corrosion to the change in the amplitude of the spectral response over time by comparison between the amplitudes of spectral responses of first and second adjacent portions;

if the contribution of the corrosion to the change in amplitude is greater, in absolute value, than a threshold value on at least one of the second portions of the metallic solid part, determining the presence of corrosion on said at least one second portion.

14. The method of claim 13, further comprising, after determining the presence of corrosion on said at least one second portion, determining the type of corrosion according to the sign of the change in amplitude.

* * * * *